US008759391B2

(12) United States Patent
Cohen et al.

(10) Patent No.: US 8,759,391 B2
(45) Date of Patent: Jun. 24, 2014

(54) TOPICAL ANESTHETIC FOR RAPID LOCAL ANESTHESIA

(75) Inventors: David M. Cohen, Lauderdale by the Sea, FL (US); Eugene R Cooper, Berwyn, PA (US)

(73) Assignee: Juventio, LLC, Chatham, NJ (US)

( * ) Notice: Subject to any disclaimer, the term of this patent is extended or adjusted under 35 U.S.C. 154(b) by 755 days.

(21) Appl. No.: 12/015,113

(22) Filed: Jan. 16, 2008

(65) Prior Publication Data

US 2008/0176948 A1    Jul. 24, 2008

Related U.S. Application Data

(60) Provisional application No. 60/885,068, filed on Jan. 16, 2007.

(51) Int. Cl.
*A61K 31/24*    (2006.01)

(52) U.S. Cl.
USPC .......................................... 514/535

(58) Field of Classification Search
USPC .......................................... 514/535
See application file for complete search history.

(56) References Cited

U.S. PATENT DOCUMENTS

| | | | |
|---|---|---|---|
| 4,091,090 A | 5/1978 | Sipos | |
| 4,552,872 A | 11/1985 | Cooper et al. | |
| 4,764,381 A | 8/1988 | Bodor et al. | |
| 5,196,410 A | 3/1993 | Francoeur et al. | |
| 5,534,242 A | 7/1996 | Henry et al. | |
| 5,534,246 A * | 7/1996 | Herb et al. ............. | 424/66 |
| 5,585,398 A | 12/1996 | Ernst | |
| 5,853,732 A | 12/1998 | Munden | |
| 6,295,469 B1 | 9/2001 | Linkwitz et al. | |
| 6,319,913 B1 | 11/2001 | Mak et al. | |
| 6,528,086 B2 | 3/2003 | Zhang | |
| 6,579,865 B2 | 6/2003 | Mak et al. | |
| 6,635,674 B1 | 10/2003 | Kaneko et al. | |
| 6,894,078 B2 * | 5/2005 | Castillo ................. | 514/626 |
| 7,273,887 B1 | 9/2007 | Wepfer | |
| 7,335,379 B2 | 2/2008 | Carrara et al. | |
| 7,504,114 B1 | 3/2009 | Kurita et al. | |
| 2003/0027833 A1 | 2/2003 | Cleary et al. | |
| 2004/0131665 A1 | 7/2004 | Wepfer | |
| 2005/0014823 A1 | 1/2005 | Soderlund et al. | |
| 2005/0276842 A1 | 12/2005 | Zhang et al. | |
| 2006/0280783 A1 | 12/2006 | Dipietro et al. | |
| 2007/0189978 A1 | 8/2007 | Zhang et al. | |
| 2007/0269393 A1 | 11/2007 | Wepfer | |
| 2009/0048347 A1 | 2/2009 | Cohen et al. | |
| 2010/0016442 A1 | 1/2010 | Cohen et al. | |

FOREIGN PATENT DOCUMENTS

| | | |
|---|---|---|
| CA | 2446060 A1 | 11/2002 |
| EP | 1293203 A1 | 3/2003 |
| WO | 2007031753 A2 | 3/2007 |
| WO | 2007038325 A2 | 4/2007 |
| WO | 2007070679 A2 | 6/2007 |
| WO | 2007070695 A2 | 6/2007 |
| WO | 2009026178 A2 | 2/2009 |

OTHER PUBLICATIONS

Rodu et al. (J Oral Pathol., vol. 17, Nos. 9-10, Abstract; 1988).*
Galinsky et al. ["Basic Pharmacokinetics and Pharmacodynamics." in: Remington: The Science and Practice of Pharmacy (Baltimore, Lippincott Williams & Wilkins, 2006), p. 1171].*
Cooper, E., "Vehicle Effects on Skin Penetration," Percutaneous Absorption, R. L. Bronaugh and H. I. Maibach, Eds., Marcel Dekker, Inc., New York, 525-529 (1985).
Cooper, E.R., "Increased Skin Permeability for Lipophilic Molecules," J. Pharm. Sci., 73(8):1153-1156 (1984).
Cooper, E.R., et al., "Effect of Fatty Acids and Alcohols on the Penetration of Acyclovir Across Human Skin In Vitro," J. Pharm. Sci., 74(6):688-689 (1985).
Cooper, E.R., et al., "Skin Permeability," Methods in Skin Research, D. Skerrow and C.J. Skerrow, Eds., John Wiley and Sons, Chichester, 407-432 (1985).
Material Safety Data Sheet Cyclohexylmethanol, 99%. Fisher Scientific [online], Mar. 7, 2006 [retrieved on Apr. 20, 2008] Retrieved from the internet URL:<https://fscimage.fishersci.com/msds/46753.htm>.
Merritt, E.W., et al., "Diffusion Apparatus for Skin Penetration," J. Controlled Release, 1:161-162 (1984).
Vaida, et al., "Prolongation of lidocaine spinal anesthesia with phenylephrine," Anesthesia and Analgesia, 65(7):781-785 (1986).
Williams, et al., "Benzyl Alcohol Attenuates the Pain of Lidocaine Injections and Prolongs Anesthesia," J. Dermatol Surg Oncol., 20:730-733 (1994).
International Search Report for PCT/US08/51176 dated May 20. 2008.
United States District Court Southern District of Florida, Case No. 09-cv-60284-GRAHAM/TORRES, Complaint dated Feb. 20, 2009.
United States District Court Southern District of Florida, Case No. 09-cv-60284-GRAHAM/TORRES, Defendant's Answer to Plaintiff's Complaint with Affirmative Defenses and Counterclaim dated Mar. 23, 2009.
International Search Report for PCT/US2009/004173 dated Dec. 7, 2009.
United States District Court Southern District of Florida, Case No. 09-cv-60284-GRAHAM/TORRES, Condensed Transcript of Confidential Deposition dated Mar. 11, 2009.
United States District Court Southern District of Florida, Case No. 09-cv-60284-GRAHAM/TORRES, Settlement Agreement and Release dated Sep. 11, 2009.

* cited by examiner

*Primary Examiner* — Kevin E Weddington
(74) *Attorney, Agent, or Firm* — Hoffman & Baron, LLP

(57) ABSTRACT

A topical anesthetic for rapid local anesthesia is provided. The topical anesthetic includes an anesthetic, volatile and non-volatile solvents, and a thickener. In addition, a method is taught for applying the topical anesthetic to the face of a patient without occlusion. The anesthetic is applied topically to an area for injection such that the dermatological procedure (cosmetic injections) can be performed in fifteen minutes.

15 Claims, No Drawings

TOPICAL ANESTHETIC FOR RAPID LOCAL ANESTHESIA

CROSS-REFERENCE TO RELATED APPLICATIONS

This application claims the benefit of U.S. Provisional Application No. 60/885,068, filed Jan. 16, 2007.

STATEMENT REGARDING FEDERALLY SPONSORED RESEARCH OR DEVELOPMENT

Not Applicable

THE NAMES OF PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The invention relates to topical anesthetics and methods for applying such anesthetics.

2. Description of the Related Art

Before performing dermatological treatments, the patient is locally anesthetized with topical anesthetics. Existing topical anesthetics used on the face take up to an hour to anesthetize effectively. The delay between application and effective anesthesia causes waiting room delays in a medical office. In addition, an impatient physician may want to begin a procedure before the patient is fully anesthetized Thus, there exists a need to quicken the action of topical anesthetics.

BRIEF SUMMARY OF THE INVENTION

It is accordingly an object of the invention to provide a topical anesthetic for rapid (less than one hour) local anesthesia.

With the foregoing and other objects in view there is provided, in accordance with the invention, a topical anesthetic for rapid local anesthesia. The topical anesthetic includes an anesthetic, a volatile solvent, and a non-volatile solvent.

The anesthetic can be a parenteral-local anesthetic such as lidocaine. The anesthetic concentration is four to eight weight percent. Solutions of up to four percent are preferable because the U.S. Food and Drug Administration is expected to limit the concentration for over-the-counter use to four percent of lidocaine.

Parenteral-local anesthetics cause loss of feeling before and during surgery, dental procedures (including dental surgery), or labor and delivery. These medicines do not cause loss of consciousness. Examples of parenteral-local anesthetics include articaine, bupivacaine, chloroprocaine, etidocaine, levobupivacaine, lidocaine, mepivacaine, prilocaine, procaine, and tetracaine. In the United States, these anesthetics are sold under the following trade names: CARBOCAINE6, CARBOCAINE WITH NEO-COBEFRIN6, CHIROCAINE10, CITANEST FORTE7, CITANEST PLAIN7, DALCAINE5, DILOCAINE5, DURANEST4, DURANEST-MPF4, ISOCAINE6, L-CAINE5, LIDOJECT-15, LIDOJECT-25, MARCAINE2, MARCAINE SPINAL2, NESACAINE3, NESACAINE-MPF3, NOVOCAIN8, OCTOCAINE5, POLOCAINE6, POLOCAINE-MPF6, PONTOCAINE9, SENSORCAINE2, SENSORCAINE-MPF2, SENSORCAINE-MPF SPINAL2, SEPTOCAINE1, XYLOCAINE5, XYLOCAINE-MPF5, and XYLOCAINE-MPF WITH GLUCOSE5. In Canada, the anesthetics are sold under the following trade names: ASTRACAINE 4%1, ASTRACAINE 4% FORTE1, CARBOCAINE6, CITANEST FORTE7, CITANEST PLAIN7, ISOCAINE 2%6, ISOCAINE 3%6, MARCAINE2, NESACAINE-CE3, NOVOCAIN8, OCTOCAINE-505, OCTOCAINE-1005 POLOCAINE6, PONTOCAINE9, SENSORCAINE2, SENSORCAINE FORTE2, ULTRACAINE D-S1, ULTRACAINE D-S FORTE1, XYLOCAINE5, XYLOCAINE TEST DOSE5, and XYLOCAINE 5% SPINAL5.

The non-volatile solvent system includes oleyl alcohol and propylene glycol. Generally, the fatty alcohol can be a $C_{10}$ to $C_{14}$ saturated alcohol, a liquid-at-room-temperature $C_{12}$ to $C_{22}$ mono- or polyunsaturatured or branched chain alcohol, or those same compounds in acid form. The fatty alcohol forms two to six percent of the formulation by weight, and, in particular, four percent by weight of the formulation.

The other non-volatile solvent, propylene glycol or a butane diol with adjacent hydroxyl groups, forms between two and six percent by weight of the formulation.

The formulation includes a volatile, short-chain alcohol such as isopropyl alcohol (IPA) or ethanol. Short-chain alcohols include the isomers of butanol, propanol, ethanol, and methanol. The short-chain alcohol forms between sixty and eighty-five percent by weight of the formulation. A thickener can be added that is soluble in the total solvent system. A suitable thickener is hydroxypropylcellulose (HPC). The thickener can form between two and five tenths and three and five tenths percent by weight of the formulation. The HPC is sold under the trade name KLUCEL.

The formulation also can include a volatile silicone. The preferred volatile silicone is polydimethylsiloxane. The volatile silicone forms up to twenty-five percent by weight of the formulation. A suitable polydimethylsiloxane is sold under the trademark DOW CORNING 200. Volatile silicone is odorless. In addition, volatile silicone has a low heat of evaporation so it does not create a cold sensation when evaporating after being deposited on the skin.

A thickener can be added to help hold the topical anesthetic on the site of the skin to be anesthetized. Without the thickener, the topical anesthetic would likely run off the skin. Other devices can be used to hold the topical anesthetic on the skin such as a gauze pad.

The invention also encompasses a method applying the topical anesthetic to a face of a patient without occlusion. The above-described topical anesthetic is applied to an injection site (i.e. a surface or area) on the skin of a patient. After approximately fifteen minutes, a dermatological procedure, such as a cosmetic injection, can be performed. The topical anesthetic can also be used as an anesthetic before circumcision. The topical anesthetic not only can be used to anesthetize cosmetic injection sites on or near the face, but any other suitable injection site. The topical anesthetic also can be used to numb any topical pain such as a burn, scrape, or cut.

Other features which are considered as characteristic for the invention are set forth in the appended claims.

As stated, an object of the invention is to provide a topical lidocaine formulation that provides faster local anesthesia than prior-art formulations that include four percent (4%) by weight of lidocaine. A further object is to provide a topical lidocaine formulation producing local anesthesia at least twenty percent (20%) faster than current products and lasts the duration of a subsequent procedure.

The resulting topical lidocaine gel has the following qualities. The topical anesthetic gel is a clear to translucent viscous gel that remains on the area of application while not leaving a film that can be easily wiped off prior to injection.

The topical anesthetic gel provides maximum local anesthesia within fifteen to twenty minutes without occlusion. The local anesthesia allowing for mild-to-deep dermal implantation of dermal fillers such as hyaluronic acid gels (such as those sold under the trademark RESTYLANE by HA North American Sales AB) and Botulinum Toxin Type A (such as those sold under the trademark BOTOX Purified Neurotoxin Complex by Allergan, Inc.). It is also believed that the topical anesthetic gel provides sufficient local anesthesia for various dermatological office procedures such as skin biopsies and removal of pre-cancerous lesions, moles, etc.

Topical anesthetic formulations that contain four percent by weight of lidocaine have been found to be effective as an external analgesic for topical anesthesia by the Food and Drug Administration (Federal Register, Volume 48, Number 27). The topical anesthetic gel described previously is specially formulated to penetrate intact skin without occlusion, for the rapid relief of pain caused by minor skin irritations, minor burns, minor cuts, and insect bites as well as topical anesthesia for dermatological procedures.

In accordance with the objects of the invention a topical anesthetic gel is provided. The topical anesthetic gel includes lidocaine in concentrations from 1% to 10% by weight in a drug delivery base composed of propylene glycol, unsaturated fatty alcohols, thickeners, isopropyl alcohol and other volatile components that have been proven safe for topical administration.

A typical package is a tube that holds two grams (2.0 g). The tube is single use for application to an individual patient.

Although the invention is illustrated and described herein as embodied in a topical anesthetic for rapid local anesthesia and a method of applying a topical anesthetic, it is nevertheless not intended to be limited to the details shown, because various modifications and structural changes may be made therein without departing from the spirit of the invention and within the scope and range of equivalents of the claims.

The construction and method of operation of the invention, however, together with additional objects and advantages thereof will be best understood from the following description of specific embodiments.

BRIEF DESCRIPTION OF THE SEVERAL VIEWS OF THE DRAWING

Not Applicable.

DETAILED DESCRIPTION OF THE INVENTION

Referring now to the composition and the Examples (which are given as non-limiting examples) thereof, there is seen a preferred embodiment of the topical anesthetic (all percentages given throughout the application are weight percentages unless otherwise specified):
 4% lidocaine
 4% propylene glycol (PG)
 4% oleyl alcohol (OA)
 3% KLUCEL (HPC)
 68% isopropyl alcohol (IPA)
 17% Dow Corning 200 volatile silicone (DC200)

The ingredients in the preferred embodiment have been found to make an effective product when in the following approximate ranges:

| | |
|---|---|
| 4%-8% | lidocaine |
| 2%-7% | OA |
| 2%-8% | PG |
| 2.5%-3.5% | KLUCEL |
| 60%-85% | IPA |
| 0%-25% | DC200 |

The ingredients in the preferred embodiment may be substituted:
 OA any saturated $C_{10}$-$C_{14}$; any mono or polyunsaturated or branched chain greater than $C_{12}$ that is a liquid at room temperature; acid could replace oleyl alcohol
 PG butane diols with adjacent OH groups
 KLUCEL any thickener that is soluble in IPA and/or DC200
 IPA any safe short-chain alcohol such as ethanol
 DC200 other volatile silicones Fatty alcohols are aliphatic alcohols derived from natural fats and oils. They are the counterparts of fatty acids. They usually (but not always) have an even number of carbon atoms. They find use in the cosmetics and food industry. Fatty alcohols are a common component of waxes, mostly as esters with fatty acids but also as alcohols themselves. Those with common names include:
 capryl alcohol (1-octanol)—8 carbon atoms
 pelargonic alcohol (1-nonanol)—9 carbon atoms
 capric alcohol (1-decanol, decyl alcohol)—10 carbon atoms
 1-dodecanol (lauryl alcohol)—12 carbon atoms
 myristyl alcohol (1-tetradecanol)—14 carbon atoms
 palmitoleyl alcohol (cis-9-hexadecan-1-ol)—16 carbon atoms, unsaturated, $CH_3(CH_2)_5CH=CH(CH_2)_8OH$
 isostearyl alcohol (16-methylheptadecan-1-ol)—18 carbon atoms, branched, $(CH_3)_2CH-(CH_2)_{15}OH$
 elaidyl alcohol (9E-octadecen-1-ol)—18 carbon atoms, unsaturated, $CH_3(CH_2)_7CH=CH(CH_2)_8OH$
 oleyl alcohol (cis-9-octadecen-1-ol)—18 carbon atoms, unsaturated
 linoleyl alcohol (9Z, 12Z-octadecadien-1-ol)—18 carbon atoms, polyunsaturated
 elaidolinoleyl alcohol (9E, 12E-octadecadien-1-ol)—18 carbon atoms, polyunsaturated
 linolenyl alcohol (9Z, 12Z, 15Z-octadecatrien-1-ol)—18 carbon atoms, polyunsaturated
 elaidolinolenyl alcohol (9E, 12E, 15-E-octadecatrien-1-ol)—18 carbon atoms, polyunsaturated
 ricinoleyl alcohol (12-hydroxy-9-octadecen-1-ol)—18 carbon atoms, unsaturated, diol, $CH_3(CH_2)_5CH(OH)CH_2CH=CH(CH_2)_8OH$
 arachidyl alcohol (1-eicosanol)—20 carbon atoms
 behenyl alcohol (1-docosanol)—22 carbon atoms
 erucyl alcohol (cis-13-docosen-1-ol)—22 carbon atoms, unsaturated, $CH_3(CH_2)_7CH=CH(CH_2)_{12}OH$
 lignoceryl alcohol (1-tetracosanol)—24 carbon atoms
 ceryl alcohol (1-hexacosanol)—26 carbon atoms
 montanyl alcohol, cluytyl alcohol (1-octacosanol)—28 carbon atoms
 myricyl alcohol, melissyl alcohol (1-triacontanol)—30 carbon atoms
 geddyl alcohol (1-tetratriacontanol)—34 carbon atoms Alternatives to the isopropyl alcohol in the formulation could be ethanol.

Propylene glycol, known also by the systematic name propane-1,2-diol, is an organic compound (a diol), usually a tasteless, odorless, and colorless clear oily liquid that is hygroscopic and miscible with water, acetone, and chloroform. It is manufactured by the hydration of propylene oxide.

For the KLUCEL (hydroxypropylcellulose), there are a number of pharmaceutical grades that vary in molecular weight.

For the volatile silicone, there are a number of compounds that are similar.

EXAMPLES

Two lidocaine formulations are being evaluated. Formulation #1 contains 3% KLUCEL. Formulation #2 contains 2% KLUCEL.

Both formulations are clear to translucent liquids. Formulation #1 is slightly thicker than Formulation #2 but both are sufficiently viscous so as not to drip when applied.

Product is placed around the area of the lips with a cotton swab and then rubbed into the area.

Patient #1—Formulation #1—experienced numbness almost immediately and was able to be injected after 15 minutes exposure. No pain due to the needle stick was noted.

Patient #2—Formulation #2—experienced numbness almost immediately and was able to be injected after 15 minutes exposure. Patient indicated that the pain at injection was similar to previous procedures that utilized EMLA. However, previous procedures allowed the EMLA to remain on the skin for over 60 minutes prior to injection.

Patient #3—Formulation #1—two applications 15 minutes apart were made. Patient experienced pain on injections similar to previous injections. Again, previous procedures utilized EMLA and greater than 60 minutes exposure.

Patient #4—Formulations #1 and #2—Products were applied to the left and right side of the site to evaluate the products side-by-side. Formulation #1 was judged superior by the patient, faster numbness. Injections were made 15 to 20 minutes after application.

Two additional patients were evaluated. Samples were applied as per Patient #4 above. In both cases, Formulation #1 was judged superior. In addition, one patient that required removal of a growth was treated with Formulation #1 and after 15 minutes, had no pain at the site of biopsy.

While various descriptions of the present invention are described above, it should be understood that the various features could be used singly or in any combination thereof. Therefore, this invention is not to be limited to only the specifically preferred embodiments depicted herein.

Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A topical anesthetic for rapid local anesthesia, comprising:
   up to four weight percent of an anesthetic agent;
   from sixty to eighty five weight percent isopropyl alcohol;
   between two and six weight percent propylene glycol;
   from two to six weight percent oleyl alcohol;
   up to 25 weight percent of volatile silicone; and
   hydroxypropylcellulose.

2. A topical anesthetic composition for delivery of rapid local anesthesia comprising:
   (a) a topical anesthetic;
   (b) a solvent system comprising:
      (i) a first non-volatile solvent comprising 2- 6% by weight of a fatty alcohol or acid selected from the group consisting of (1) $C_{10}$-$C_{14}$ saturated alcohols or their corresponding acids and (2) liquid-at-room temperature $C_{12}$-$C_{22}$ mono- or poly-unsaturated or branched alcohols or their corresponding acids;
      (ii) a second non-volatile solvent comprising 2- 6% by weight of an alcohol selected from the group consisting of propylene glycol and butane diols with adjacent OH groups; and
      (iii) a volatile short chain alcohol;
   wherein the composition penetrates intact skin without occlusion to effectuate maximum local anesthetic affect within 15 to 20 minutes.

3. The topical anesthetic composition of claim 2, wherein said anesthetic is present in amounts of about 4 to about 8 percent by weight.

4. The topical anesthetic composition of claim 3, wherein said anesthetic comprises lidocaine.

5. The topical anesthetic composition of claim 2, wherein said anesthetic is selected from the group consisting of articaine, bupivacaine, chloroprocaine, etiodocaine, levobupivacaine, lidocaine, mepivacaine, prilocaine, procaine and tetracaine.

6. The topical anesthetic composition of claim 2, wherein the first non-volatile solvent comprises oleyl alcohol.

7. The topical anesthetic composition of claim 2, wherein the short chain alcohol comprises isopropyl alcohol.

8. The topical anesthetic composition of claim 2, further comprising a volatile silicone.

9. The topical anesthetic composition of claim 2, further comprising a thickener.

10. The topical anesthetic composition of claim 2, wherein the composition is a gel.

11. A topical anesthetic composition for rapid delivery of a local anesthesia comprising:
   (a) a topical anesthetic comprising lidocaine;
   (b) a solvent system comprising:
      (i) a first non-volatile solvent comprising 2- 6% by weight of a fatty alcohol comprising oleyl alcohol;
      (ii) a second non-volatile solvent comprising 2- 6% by weight of an alcohol comprising propylene glycol; and
      (iii) a volatile short chain solvent;
   wherein the composition penetrates intact skin without occlusion to effectuate maximum local anesthetic effect within 15 to 20 minutes.

12. The topical anesthetic composition of claim 11, wherein the short chain alcohol is isopropyl alcohol.

13. The topical anesthetic composition of claim 11, further comprising a volatile silicone.

14. The topical anesthetic composition of claim 11, further comprising a thickener.

15. The topical anesthetic composition of claim 14, wherein said thickener is present in an amount sufficient to produce a gel.

* * * * *